US010478263B2

(12) United States Patent
Allmendinger et al.

(10) Patent No.: US 10,478,263 B2
(45) Date of Patent: Nov. 19, 2019

(54) DISPLACEMENT CONTROL WIRE DEVICE AND METHOD

(71) Applicant: Northeast Scientific, Inc., Waterbury, CT (US)

(72) Inventors: Craig Allmendinger, Waterbury, CT (US); Steven W. Miller, Lake Worth, FL (US)

(73) Assignee: Northeast Scientific, Inc., Waterbury, CT (US)

(*) Notice: Subject to any disclaimer, the term of this patent is extended or adjusted under 35 U.S.C. 154(b) by 95 days.

(21) Appl. No.: 14/878,757

(22) Filed: Oct. 8, 2015

(65) Prior Publication Data

US 2016/0120614 A1 May 5, 2016

Related U.S. Application Data

(60) Provisional application No. 62/061,334, filed on Oct. 8, 2014.

(51) Int. Cl.
| | |
|---|---|
| *A61B 90/00* | (2016.01) |
| *A61B 17/02* | (2006.01) |
| *A61B 18/00* | (2006.01) |
| *A61B 17/00* | (2006.01) |

(52) U.S. Cl.
CPC .......... *A61B 90/04* (2016.02); *A61B 17/0218* (2013.01); *A61B 2017/003* (2013.01); *A61B 2017/00818* (2013.01); *A61B 2018/00577* (2013.01); *A61B 2090/0427* (2016.02)

(58) Field of Classification Search
CPC ................ A61B 90/04; A61B 17/0218; A61B 2017/00818; A61B 2017/003; A61B 2018/00577; A61B 2018/209; A61B 2018/0427; A61M 2025/0161
USPC ....................................................... 606/21, 191
See application file for complete search history.

(56) References Cited

U.S. PATENT DOCUMENTS

| | | | |
|---|---|---|---|
| 6,067,990 A | 5/2000 | Kieturakis | |
| 6,259,938 B1* | 7/2001 | Zarychta | A61B 5/0421 600/380 |
| 7,621,908 B2 | 11/2009 | Miller | |
| 8,529,443 B2 | 9/2013 | Maloney | |
| 2006/0135961 A1* | 6/2006 | Rosenman | A61M 25/0045 606/108 |
| 2008/0033415 A1* | 2/2008 | Rieker | A61M 25/0147 606/21 |

(Continued)

*Primary Examiner* — Kaylee R Wilson
(74) *Attorney, Agent, or Firm* — McHale & Slavin, P.A.

(57) ABSTRACT

The present invention provides a device and method for displacing a lumen within a patient in-vivo during a surgical procedure. More specifically, the present disclosure relates to displacement control wires used in a heart ablation procedure for biasing a patient body portion, e.g., a wall of an esophagus away from or closer to the heart to prevent damage to the esophagus as a result of the heart ablation. The control wire is constructed from a shape memory material such as nitinol. The nitinol material is constructed and arranged to be substantially straight when cooled for insertion. Thereafter, when inserted into the body, the nitinol material takes on a curved orientation (preformed) as it is heated to body temperature. Rotation of the control wire allows the esophagus to be displaced as desired for the procedure.

17 Claims, 8 Drawing Sheets

(56) References Cited

U.S. PATENT DOCUMENTS

| | | | | |
|---|---|---|---|---|
| 2010/0030098 A1* | 2/2010 | Fojtik | ................... | A61B 5/015 |
| | | | | 600/549 |
| 2011/0040314 A1* | 2/2011 | McGuckin, Jr. | ....... | A61B 17/22 |
| | | | | 606/159 |
| 2011/0282338 A1* | 11/2011 | Fojtik | ................... | A61M 29/02 |
| | | | | 606/33 |

* cited by examiner

FIG. 12

DISPLACEMENT CONTROL WIRE DEVICE AND METHOD

PRIORITY CLAIM

In accordance with 37 C.F.R. 1.76, a claim of priority is included in an Application Data Sheet filed concurrently herewith. Accordingly, the present invention claims priority to U.S. Provisional Patent Application No. 62/061,334, entitled "Displacement Control Wire Device and Method", filed Oct. 8, 2014. The contents of the above referenced application are incorporated herein by reference in its entirety.

BACKGROUND

Catheters for manipulation of the esophagus are known in the art. For example, U.S. Pat. No. 7,621,908 to Miller, incorporated by reference herein, describes a catheter for manipulation of the esophagus that uses a control wire associated with a catheter tube, the control wire changing the shape of the catheter and displacing the esophagus relative to the heart to reduce the risk of an esophageal fistula resulting from atrial radio frequency (RF) ablation. In relevant part, this reference requires use of a pair of control wires and/or a control wire utilizing a curved portion to manipulate the catheter to move the esophagus.

As is described by Miller, the goal of the surgical treatment of atrial fibrillation is to block or interfere with impulses radiating from ectopic foci inside the pulmonary veins that triggered atrial fibrillation. Among the first intra-heart surgical treatments for atrial fibrillation was demonstrated by the Leipzig group in a procedure referred to as, endocardial linear lesion, to connect the pulmonary vein to the mitral annulus during open heart surgery.

The Mayo Clinic is known for another open heart surgical procedure, termed the Maze procedure, in which multiple cuts are created in the atrial muscle in a maze pattern. These cuts produce scar tissue that does not carry electrical impulses and, as a result, the stray impulses causing atrial fibrillation are eliminated, producing a normal coordinated heartbeat.

More recently, cardiology specialists, called electrophysiologists, have used cardiac catheters to ablate the heart tissue without the need for open heart surgery. In this procedure, an RF catheter is inserted into the atrium and a series of ablations or burns are performed around the mouth of the pulmonary vein and the left atrial wall. The ablations also form scar tissue, blocking stray electrical impulses to restore normal heartbeat. During RF catheter ablation, lesion depth, extension and volume are related to the design of the ablation electrode and the RF power delivered.

Among the complications that may arise is pulmonary vein stenosis if the ablations are too close to the mouth of the pulmonary vein. Another serious, and possibly fatal, complication is atrial-esophageal fistula caused by thermal penetration of the walls of the atrium and esophagus. The atrial-esophageal fistula can lead to pericarditis, or fluid between the outer wall of the heart and the pericardium, restricting the heartbeat, hemorrhage, or other life threatening conditions.

The atrial-esophageal fistula, or hole, in the esophageal wall may result, in part, from simple anatomy and the RF power needed to develop ablations, as well as the design of the catheter electrode tip and other contributing factors such as movement of the esophagus during the procedure.

The esophagus is located at the center of the posterior mediastinum and is separated from the atrium only by the pericardial sac and/or a thin layer of fatty tissue, and may be in contact with the atrium. The left atrium wall thickness is about 2-4 mm, and the esophagus 10 thickness is about 2-3 mm. The esophagus 10 is supported at its upper end near the trachea 21 and transits the diaphragm 22 to connect with the stomach. The esophagus 10 is supported at its lower end by the diaphragm 22. The thoracic portion 9 of the esophagus 10, between the trachea 21 and the diaphragm 22, is mobile and loosely restrained only by soft tissue. This allows the esophagus to move in response to swallowing food, cardiac and lung movement, as well as upper body movements. This flexibility of the esophagus complicates the problem of avoiding atrial-esophageal fistula.

Currently, several techniques are employed by the electrophysiologists to reduce the likelihood of an atrial-esophageal fistula developing during the RF atrial ablation. The most comprehensive technique involves a pre-operative procedure of developing a 3-D map of the operative field by CT scan or MRI displayed with real time 3-D electroanatomical maps to reveal the cardiac anatomical relationships. This mapping system may, or may not, be used with a contrast medium in the esophagus to better locate the position of the esophagus. The mapping systems allow the ablations to be precisely plotted on the atrium wall. The locations of some ablations may be changed or adjusted because of anatomical considerations. Contrast placement in the esophagus may be used independently of CT/MRI to allow real time visualization of the esophagus.

Thus, in some cases, the area of the atrium traversed by the esophagus is avoided during the ablation procedure to reduce or eliminate the risk of damaging the esophagus. In these cases, the success of the surgery may be compromised due to the skipped area of ablation.

Other methods utilized to reduce the risk of damage to the esophagus include reducing the electrical energy of the electrode in the vicinity of the esophagus. However, the adjustment is not significant and damage may still occur. In addition, the efficacy of the procedure may be compromised.

Figure 1:
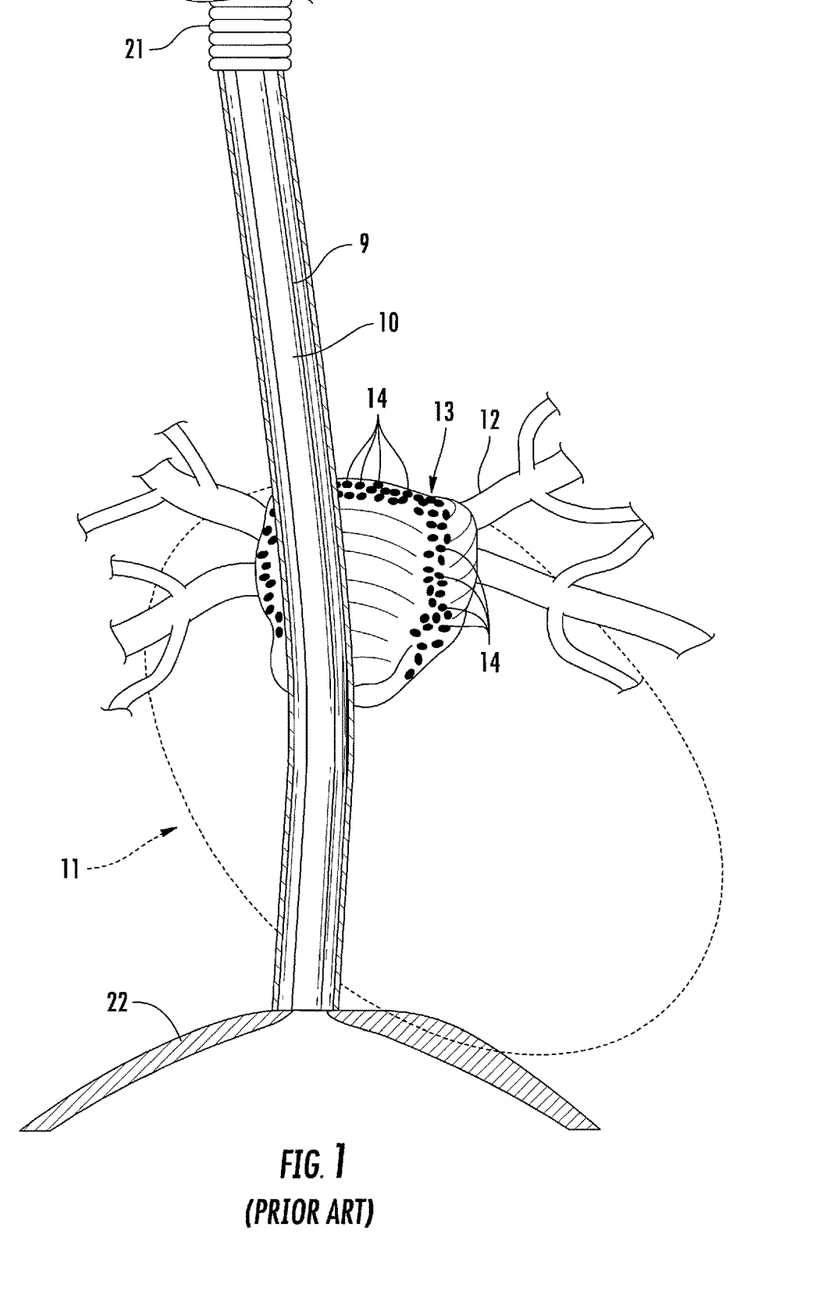
FIG. 1 is a representation of the heart and esophagus showing a pattern of optimal ablation lesions.

PRIOR ART FIG. 1, from Miller, illustrates a posterior view of the patient shown with the heart 11 in phantom lines lying in front of the esophagus 10. The esophagus is supported by the trachea 21 at one end and by the diaphragm 22 at the other end. Normal anatomical variation in the exact location of the atrium-esophageal relationship does occur. The right pulmonary vein 12 enters the atrium 13, and the desired pattern of optimal ablation lesions 14 are shown as they might appear in the mapping procedure. When viewing these proposed ablation lesions 14, either pre-operatively or intra-operatively, the surgeon may decide to change the location of some of the ablations because of the proximity to the esophagus 10. If a particular ablation(s) is considered necessary, regardless of the location of the esophagus, the RF power to the electrode may be reduced.

Figure 2:
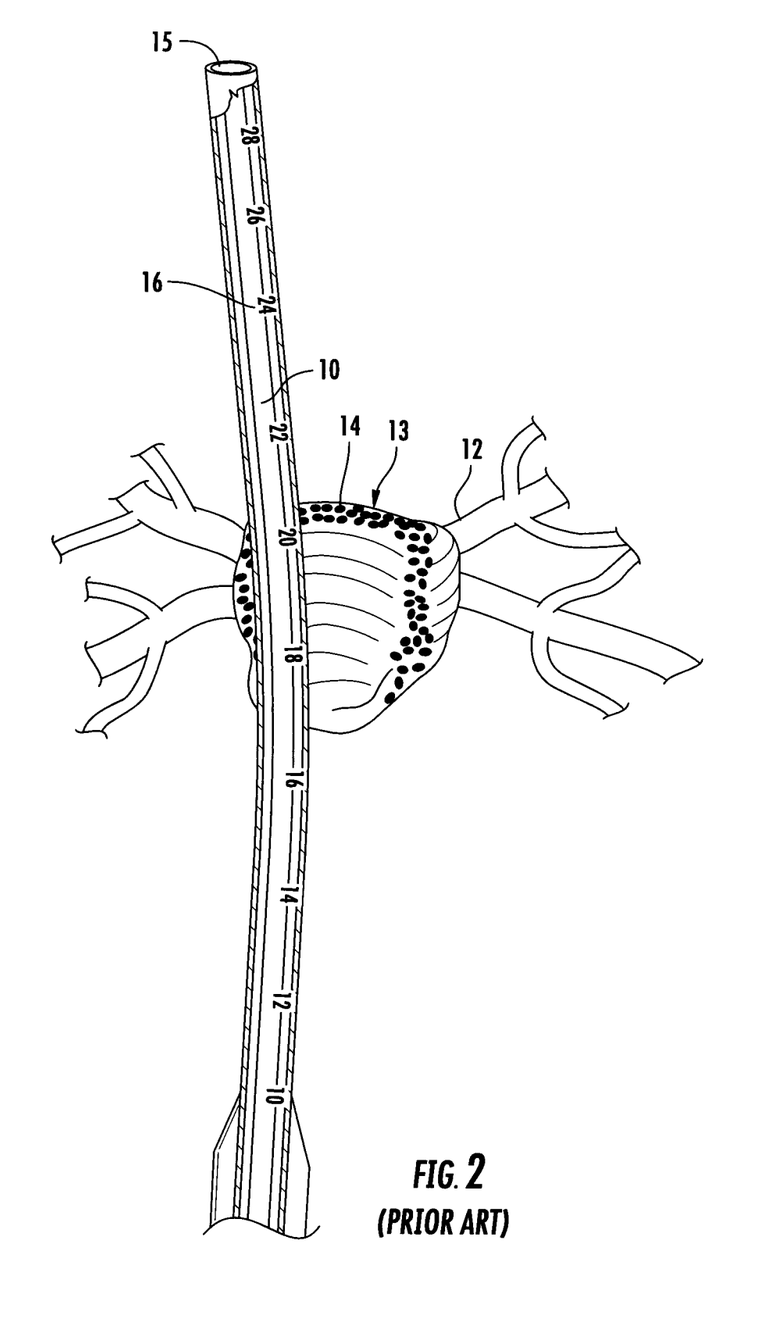
FIG. 2 is a representation of the heart and esophagus of PRIOR ART FIG. 1 with an esophageal catheter inserted.

To manage the surgical field, to eliminate the possibility of an esophageal fistula, an esophageal catheter or tube 15 is inserted through the mouth or nose into the esophagus 10 and through the length of the esophagus past the diaphragm 22, as shown in PRIOR ART FIG. 2. The catheter 15 may include a radiologic marker or markers 16 to improve visualization of the location of the catheter 15 and esophagus 10.

Figure 3:
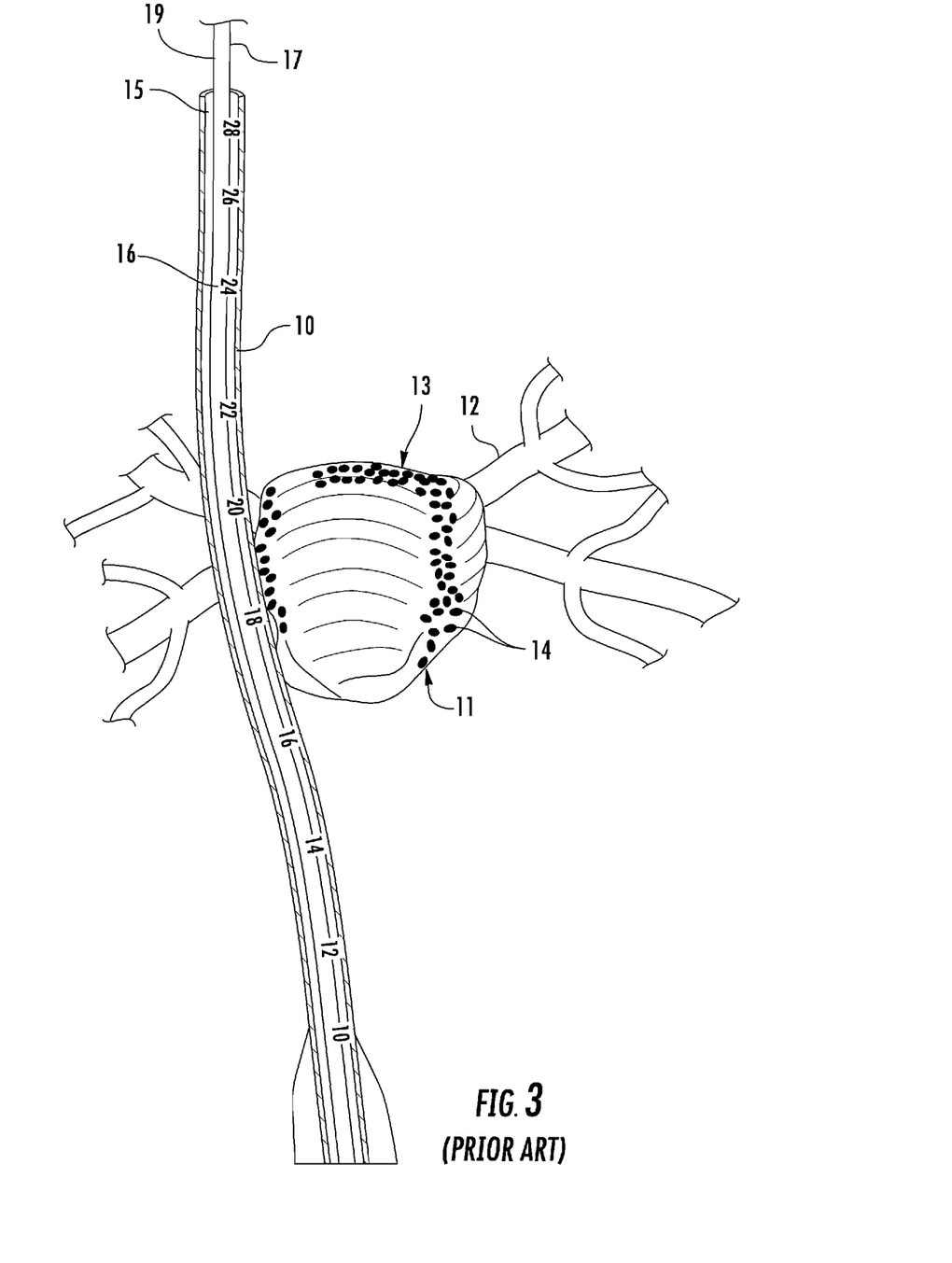
FIG. 3 is a representation of the heart and esophagus of PRIOR ART FIG. 1 with the control wires changing the direction of the catheter and esophagus.
Figure 4:
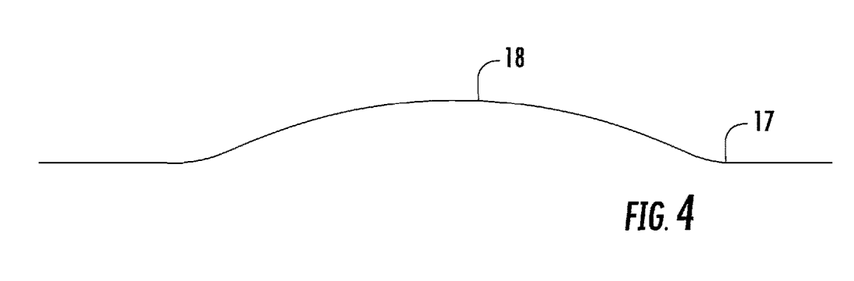
FIG. 4 is a representation of one of the control wires of PRIOR ART FIG. 3.
Figure 5:
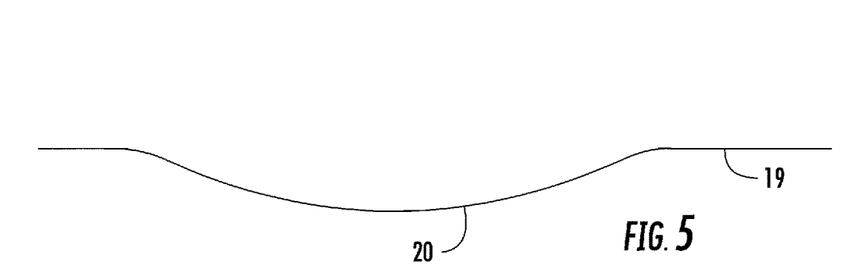
FIG. 5 is a representation of another of the control wires of PRIOR ART FIG. 3.

To move the esophagus laterally in the surgical field, and to fix the displaced portion of the esophagus beyond the area of thermal lesions, a control wire 17 is inserted through the lumen of the catheter 15. As shown in PRIOR ART FIGS. 4 and 5, the control wires have a preformed curved intermediate portion 18, 20. As the curved portion moves through the catheter, the catheter is displaced along its longitudinal axis to follow the curve of the control wire. The control wire may be round, flattened, single strand or multi-strand, such as a guide wire. The control wire 17 is manipulated within the catheter to place the curved portion 18 near the atrium and to rotate the control wire to displace the catheter and esophagus away from the ablation lesions 14, laterally and posteriorly as the patient's anatomy permits, as shown in PRIOR ART FIG. 3. Depending on the relative size of the catheter lumen 27 and the control wire, a second control wire 19 having a similar curved portion 20 may be used. The control wires 17 and 19 may be used in conjunction with each other to produce one curve or, independently, to form the catheter in other shapes. The use of separate control wires allows the catheter to remain in place, once inserted, and to be bent in the area dictated by the anatomy of each individual patient. As shown in PRIOR ART FIG. 3, the curvature of the catheter is left lateral, however, the control wires may be manipulated to force the esophagus in the dorsal direction away from the heart or to the right laterally.

Figure 6:
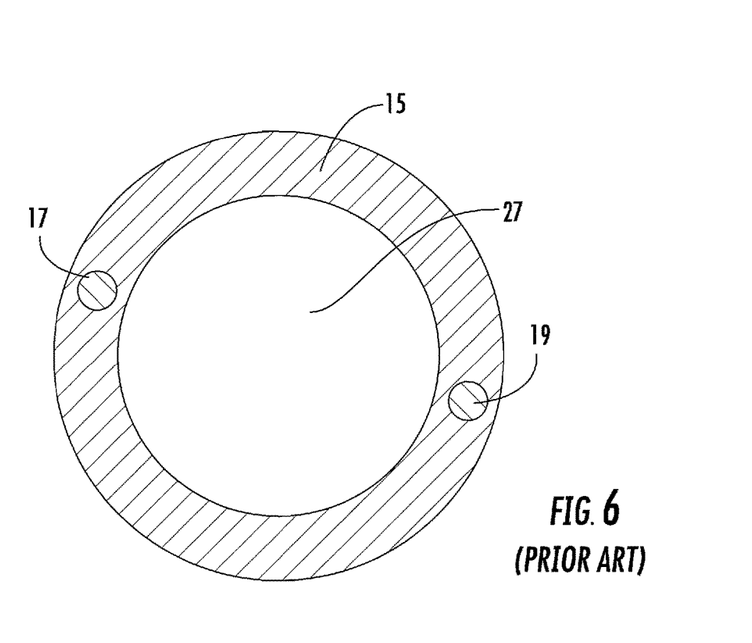
FIG. 6 is a cross section of another esophageal catheter with control wires in the sidewall.
Figure 7:
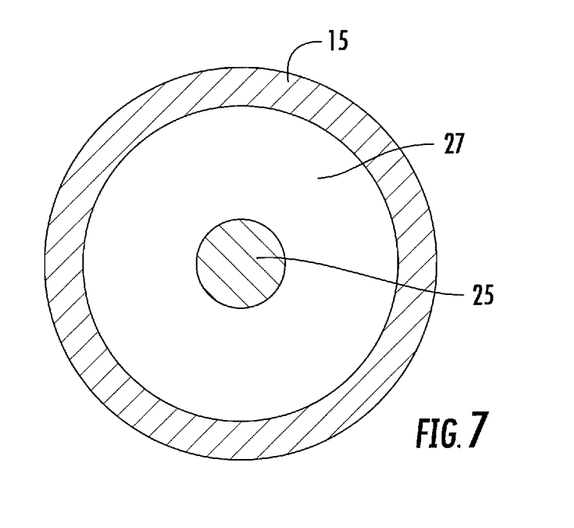
FIG. 7 is a cross section of the esophageal catheter with the control wire in the lumen.
Figure 8:
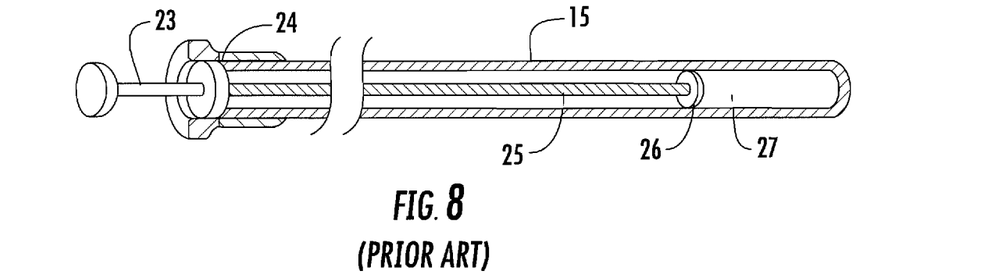
FIG. 8 is a partial longitudinal cross section of another embodiment of the esophageal catheter and control wire.

As shown in PRIOR ART FIGS. 6-8, the catheter 15 has control wires 17 and 19 attached to the sidewall at discrete points 26 along the catheter. By differential movement of the control wires and the catheter, respectively, as shown in PRIOR ART FIG. 8, the longitudinal shape of the catheter can be changed. In PRIOR ART FIG. 8, either the plunger 23 or the barrel 24 is moved relative to the other, thereby shortening one member in relation to the other and causing the catheter to bend in the mid-portion. In PRIOR ART FIG. 6, separate control wires 17 and 19 located in the sidewall of the catheter 15 can be moved to bend the catheter in different directions. In PRIOR ART FIG. 7 the control wire 25 is located in the lumen 27 and attached to the sidewall at 26. The catheter may be rotated in the esophagus to move the esophagus, as desired.

As we noted above, in relevant part, Miller requires use of a pair of control wires and/or a control wire utilizing a curved portion to manipulate the catheter to move the esophagus.

U.S. Pat. No. 5,170,803 to Hewson et al., incorporated by reference herein, describes a similar device that uses a looped wire provided as a hinge in order to manipulate the catheter for biasing the esophagus.

While these prior devices do manipulate associated catheters, their complexity raises issues with cost, reliability, reusability, etc. due to the force required to displace the catheter. Catheters having a high degree of flexibility are extremely difficult to insert into the human anatomy. Adding rigidity to the catheter for insertion severely hampers the ability of the wires to suitably displace the esophagus.

Thus, the invention provides a control wire for surgical procedures, which overcomes the disadvantages of the prior art control wires. The control wire of the present invention provides a control wire that can be utilized without a sheath to reduce the force needed to displace the anatomy as desired. The present control wire also provides easier manipulation and guidance to the user as to the direction of the manipulation.

SUMMARY

Briefly, the present invention provides a device and method for displacing a lumen within a patient in-vivo during a surgical procedure. More specifically, the present disclosure relates to displacement control wires used in a heart ablation procedure for biasing a patient body portion, e.g., a wall of an esophagus away from or closer to the heart to prevent damage to the esophagus as a result of the heart ablation. In exemplary embodiments, the control wire is constructed from a shape memory material such as nitinol. The nitinol material is constructed and arranged to be substantially straight when cooled for insertion. Thereafter, when inserted into the body, the nitinol material takes on a curved orientation (preformed) as it is heated to body temperature. Rotation of the control wire allows the esophagus to be displaced as desired for the procedure. Afterwards, the control wire is withdrawn from the patient.

In at least one embodiment, the nitinol control wire is initially provided within a tubular polymeric sheath such as, but not limited to, polytetraflouroethylene (PTFE). The sheath includes sufficient rigidity to maintain the nitinol control wire in a straight configuration prior to use. The sheath may be removed or retracted immediately prior to use of the control wire.

In other exemplary embodiments, the improved control wire incorporates a distal stabilizer foot having increased surface area and a rounded tip, e.g., a ball tip, to facilitate movement of the control wire within a catheter or vessel without catching, and to facilitate use within the esophagus without the catheter. The stabilizer foot also provides a surface that counters the force of moving a central portion of the lumen.

In other exemplary embodiments, the improved control wire utilizes an associated proximal handle with a pointer section to provide a user a frame of reference for displacement.

Accordingly it is an objective of the present invention to provide a control wire that is suitable for use without a sheath.

It is a further objective of the present invention to provide a control wire that includes suitable rounded surfaces for contacting the anatomy to prevent injury to the patient during use.

It is yet a further objective of the present invention to provide a control wire that includes a stabilizer foot at the distal end of the control wire for pressing against the anatomy without perforation thereof.

It is another objective of the present invention to provide a control wire that includes a handle to allow easy manipulation of the control wire and thus the anatomy.

It is still yet another objective of the present invention to provide a control wire that includes a pointer for providing an indication to the operator regarding the manipulation direction.

Other objectives and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

BRIEF DESCRIPTION OF THE DRAWINGS

Referring now to the drawings, wherein like elements are numbered alike in the following Figures.

PRIOR ART

PRIOR ART

PRIOR ART

PRIOR ART

PRIOR ART

PRIOR ART

PRIOR ART

PRIOR ART

DETAILED DESCRIPTION

While the present invention is susceptible of embodiment in various forms, there is shown in the drawings and will hereinafter be described a presently preferred embodiment with the understanding that the present disclosure is to be considered an exemplification of the invention and is not intended to limit the invention to the specific embodiments illustrated.

Figures 9, 10:
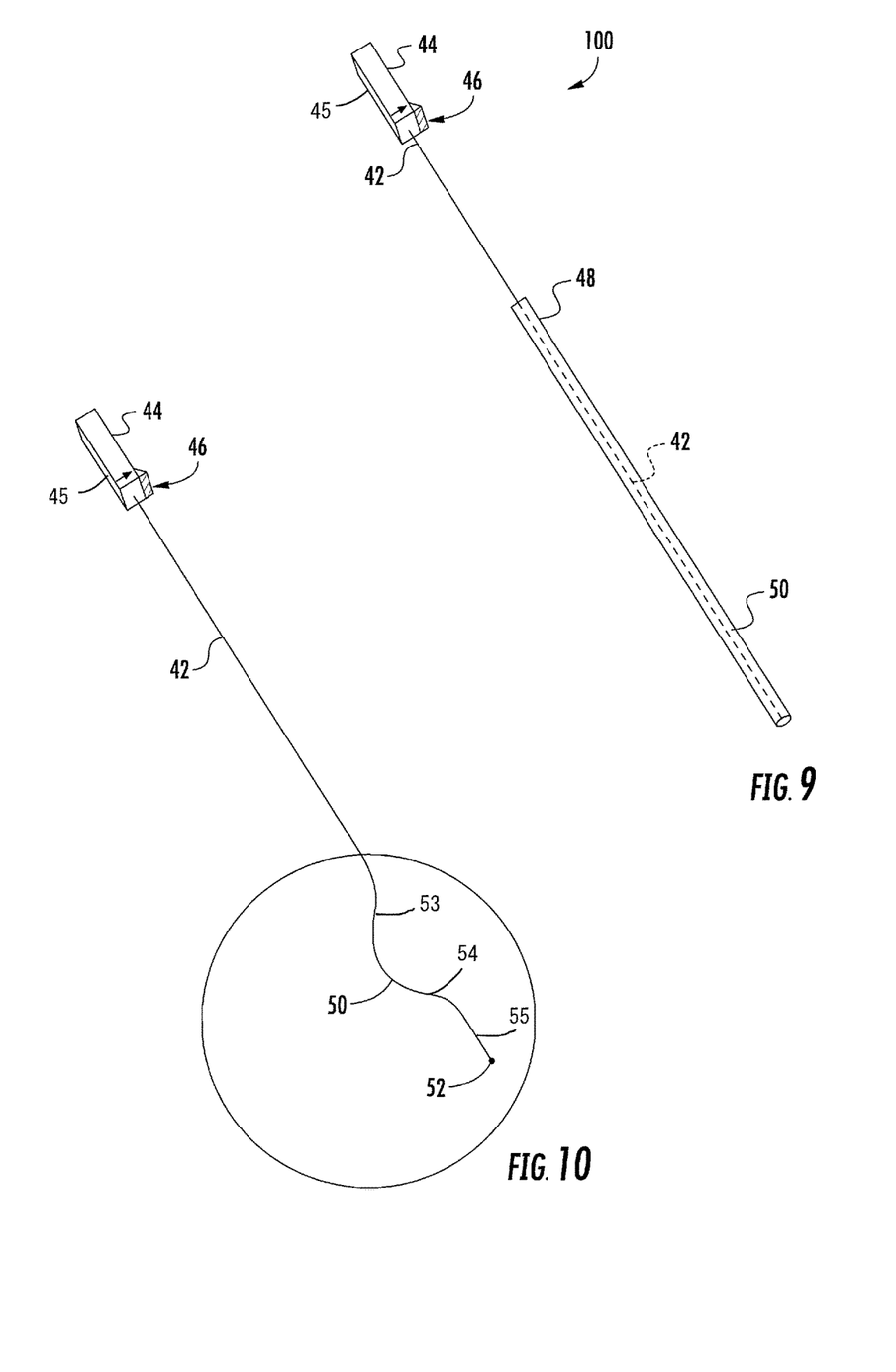
FIG. 9 is a perspective view of an exemplary control wire in a sheathed configuration.
FIG. 10 is a perspective view of the exemplary control wire of FIG. 9 in an unsheathed configuration.
Figure 11:
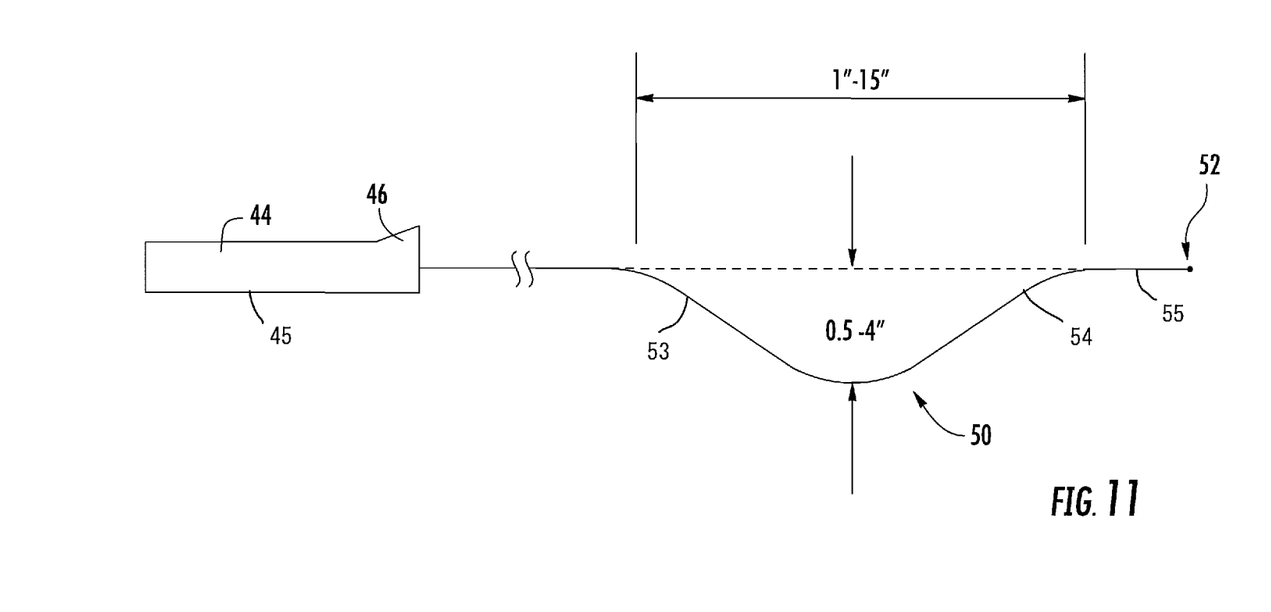
FIG. 11 is a side elevation view of an operative section of an exemplary control wire.
Figure 12:
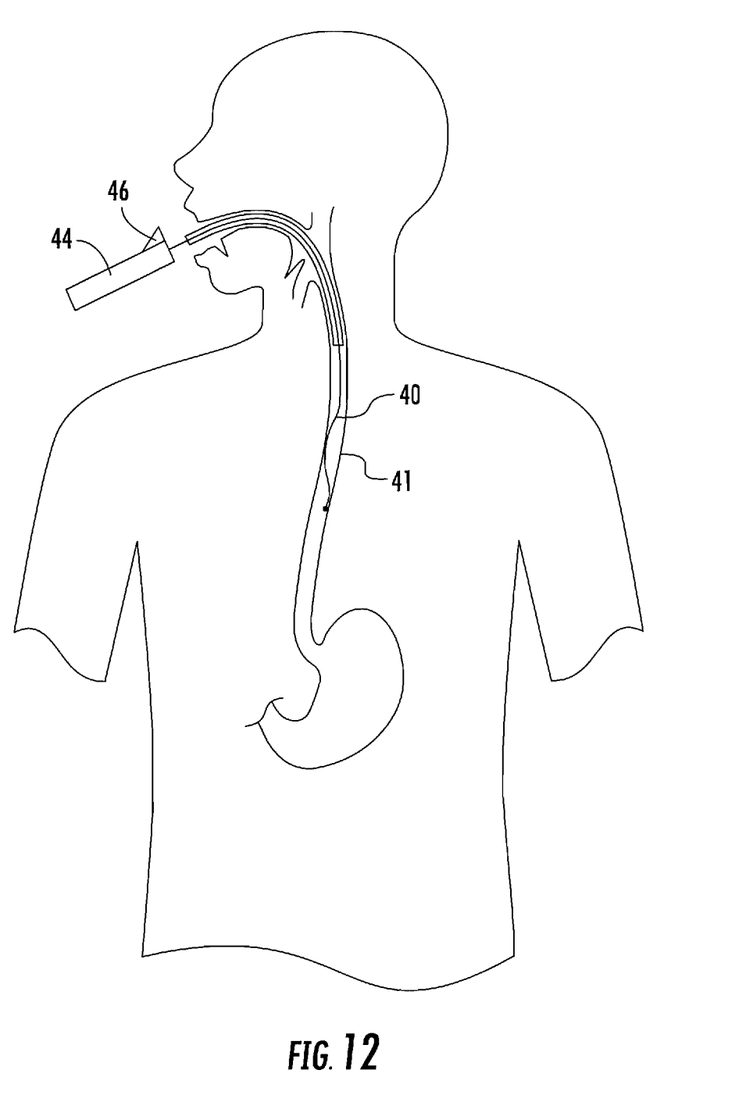
FIG. 12 is a schematic view illustrating the control wire within the human anatomy.

Referring to FIGS. 1-3 and 9-12, as was noted above, the present disclosure relates to an improved exemplary displacement control wire 100 utilizing only a single control wire for biasing a patient body portion, e.g., a wall of an esophagus 40. In exemplary embodiments, the control wire 100 is constructed from a nitinol material, which in an unused, room temperature or chilled state is straight. When the nitinol wire is inserted into the body, it takes on a curved orientation (preformed) as it is heated to body temperature. As shown in FIGS. 10-11, this curved orientation includes at least a first bend 53 and a second bend 54. In at least one embodiment, the control wire 100 is provided within a tubular sheath 50, which retains the nitinol wire in a straight configuration prior to use and provides a guideway for the control wire to pass through the mouth or sinus cavity and into the esophagus. In this manner, the sheath 50 prevents the control wire 100 from, warming, and thus curving, during insertion while simplifying the traversal of the control wire through the anatomy. Once the sheath reaches the esophagus, the control wire can be extended through the sheath, whereby it is free to interact directly with the esophageal wall 41. When it is no longer necessary to manipulate the esophagus, the control wire can be pulled out through the sheath, and the sheath can be removed or utilized for other needs. Alternatively, the control wire can be retracted into the sheath, and the sheath along with the control wire can be removed as a single unit.

In a preferred embodiment, the control wire 100 incorporates a stabilizer member 52 in the form of a spherical ball or the like on the first end portion 55. The stabilizer member 52 is constructed to have a larger surface area than that of the control wire to facilitate movement of the control wire within the sheath 50 or within the esophagus 40. The stabilizer member 52 prevents the control wire from perforating or catching the wall of the esophagus during manipulation of the wire to move the esophagus. In addition, the stabilizer member 52 provides an increased surface area on one side of the esophagus so that the curved section of the control wire can force a portion of the esophagus in an opposite direction. This construction prevents perforation of the esophagus and provides a mechanical advantage to the control wire by giving it a surface to push away from with the bend in the control wire. It should be noted that while a spherical ball is the preferred embodiment, other shapes that provide the increased surface area and prevent damage to the esophageal wall 41 while allowing the control wire to be traversed through the sheath and the anatomy may be utilized without departing from the scope of the invention.

Still referring to FIGS. 1-3 and 9-12, the improved control wire utilizes an associated handle 44 with a pointer section 46, on a second end portion 45, to provide a user a frame of reference for displacement, e.g., a pointer may be oriented away from a curve such that displacement will occur away from the pointer's direction. Alternatively, the pointer may point in the same direction of the curve without departing from the scope of the invention. The handle and pointer are preferably attached to the control wire 50 via a process such as injection molding. However, the handle and pointer may be attached with adhesive, epoxy, fasteners or the like without departing from the scope of the invention.

Referring to FIGS. 9-12, one embodiment of the control wire, generally at 40, in a sheathed configuration (before use) is illustrated. The illustrated control wire comprises a nitinol body 42 and a handle 44 including a pointer 46. A tubular sheath 48, e.g., PTFE, surrounds the body 42. While the body (or shaft) 42 of the control wire may be any diameter, one exemplary diameter useful for esophageal applications is a 0.073 inch diameter nitinol construction, with an approximate overall length of 36 inches. An operative section 50 is illustrated in a straight configuration within the sheath, see FIG. 9.

FIG. 10 illustrates the exemplary control wire of FIG. 9 in an unsheathed configuration. In this configuration, the operative section 50 takes on a curved configuration, in this exemplary case due to warming of the nitinol shaft by body tissues. An exemplary distal stabilizer member 52 facilitates movement of the shaft 42 within an associated catheter or body portion. Also, in the exemplary illustrated embodiment, the pointer 46 is provided on a handle portion opposite the curve of the operative section 50 (thus bias will be away from the side of the pointer). FIG. 11 illustrates an exemplary operative section 50 with a deviation range of between 0.5 and 4 inches, and a length of curve range of 1 to 15 inches (as exemplary ranges). FIG. 11 also shows the stabilizer member 52 at an exemplary diameter of 0.110 inches.

While exemplary embodiments are described above, the present disclosure contemplates a wide variety of alternatives. For example, metals other than nitinol that are capable of achieving a spring or spring like temper may be used, either having or not having shape memory function dependent upon temperature. For metals that do not change shape with temperature, a curve can be pre-formed and straightened using the sheath, followed by retraction of the sheath during the operation in order to induce curvature. Alternatively, the sheath may be provided with a length that extends partially through the anatomy, whereby the control wire may be extended through the sheath and into the target portion of the anatomy.

Additionally, other procedures are contemplated, wherein displacement of a vessel or other body wall may be desired, for example during cancer treatments and other surgeries.

It will be apparent to those skilled in the art that, while exemplary embodiments have been shown and described, various modifications and variations can be made to the device and method of making disclosed herein without departing from the spirit or scope of the invention. Also, the exemplary implementations described above should be read in a non-limiting fashion, both with regard to construction and methodology. Accordingly, it is to be understood that the various embodiments have been described by way of illustration and not limitation.

What is claimed is:

1. A surgical control wire comprising:
a control wire configured to provide curvature to displace a section of the esophagus of a human away from the heart during surgery, said control wire being formed of a shape memory material, said control wire having a spring temper and a suitable diameter to provide deflection of said esophagus, said control wire including a first end portion that is constructed and arranged to contact a first inner side wall of said esophagus, said first end portion including a distal end, said distal end including a stabilizer member, said stabilizer member being rounded having a surface area greater than said control wire, said stabilizer member constructed and arranged to prevent said control wire from puncturing said first inner side wall, said control wire having a first straight section adjacent said stabilizer member, an operative portion including a first bend and a second straight section in said control wire, said first bend and said second straight section configured to be large enough to force displacement of an opposite side wall of said esophagus in an opposite direction with respect to said stabilizer member, an offset bend for directing said control wire back toward a longitudinal axis of said first straight section, a second bend sized so that a shaft portion of said control wire is substantially axially aligned with said first end portion of said control wire, and a second end portion having a handle member for manipulation of said control wire, whereby rotation of said control wire mechanically displaces said section of said esophagus in the area of said esophagus containing said bends in said control wire.

2. The surgical control wire of claim 1, wherein said shape memory material is nitinol, whereby said first bend and said second bend are predetermined and configured to be formed upon warming said control wire with said esophagus.

3. The surgical control wire of claim 1, wherein said handle member includes a pointer for indicating the direction of said first bend and said second bend with respect to said pointer.

4. The surgical control wire of claim 1, wherein said stabilizer member is rounded on all corners and edges.

5. The surgical control wire of claim 4, wherein said stabilizer member is a sphere.

6. The surgical control wire of claim 1, wherein said stabilizer member is welded to said distal end of said control wire.

7. The surgical control wire of claim 1, including a sheath member constructed as a flexible tubular member having an inner lumen, said inner lumen being sized to allow passage of said control wire therethrough.

8. The surgical control wire of claim 7, wherein said inner lumen is sized to allow passage of said stabilizer member therethrough.

9. The surgical control wire of claim 8, wherein said sheath member includes a length sufficient to reach only to said esophagus while said control wire is configured to extend to said displaced section of the esophagus.

10. The surgical control wire of claim 1, wherein said control wire is round in shape.

11. The surgical control wire of claim 10, wherein said control wire has a diameter of approximately one hundred thousandths of an inch.

12. The surgical control wire of claim 1, wherein said first bend and said second bend form an offset of one to four inches.

13. The surgical control wire of claim 1, wherein said first bend and said second bend have a length of curve ranging from one to fifteen inches.

14. A surgical control wire kit comprising: a control wire, said control wire including a first end portion that is constructed and arranged to contact a first portion of an inner lumen of an esophagus of a human, said control wire being formed of a shape memory material having a spring temper and a suitable diameter to provide displacement of said esophagus, said first end portion including a distal end, said distal end including a stabilizer member, said stabilizer member having a rounded surface area greater than said control wire, said stabilizer member constructed and arranged to prevent said control wire from puncturing a first inner side wall of said esophagus, an operative portion in close proximity to said first end portion, said operative portion including an offset formed by a first bend in said control wire, said first bend configured to be large enough to force displacement of an opposite side wall of said esophagus, thereby mechanically moving a section of said esophagus in an opposite direction with respect to said stabilizer member, an offset bend to direct said control wire back toward said first inner wall, a second bend sized so that a shaft portion of said control wire is substantially axially aligned with said first end portion of said control wire, a second end portion having a handle member for manipulation of said control wire, a sheath member constructed as a flexible tubular member having an inner lumen, said inner lumen of said sheath member being sized to allow passage of said control wire therethrough.

15. The surgical control wire of claim 14, wherein said stabilizer member is rounded on all corners and edges.

16. The surgical control wire of claim 15, wherein said stabilizer member is a sphere.

17. The surgical control wire of claim 16, wherein said stabilizer member is welded to said distal end of said control wire.

* * * * *